United States Patent [19]

Osberghaus et al.

[11] 4,141,967
[45] Feb. 27, 1979

[54] COSMETIC DEODORANT PREPARATIONS CONTAINING ALKANE DIPHOSPHONIC ACID ESTERS

[75] Inventors: Rainer Osberghaus, Düsseldorf-Urdenbach; Helmut Blum, Dusseldorf, both of Fed. Rep. of Germany

[73] Assignee: Henkel Kommanditgesellschaft auf Aktien (Henkel KGaA), Dusseldorf, Fed. Rep. of Germany

[21] Appl. No.: 768,489

[22] Filed: Feb. 14, 1977

[30] Foreign Application Priority Data

Feb. 23, 1976 [DE] Fed. Rep. of Germany ....... 2607225

[51] Int. Cl.² ................................................. A61K 7/32
[52] U.S. Cl. ........................................ 424/47; 424/65; 424/204
[58] Field of Search ................................. 424/47, 204

[56] References Cited

U.S. PATENT DOCUMENTS 3,251,907  5/1966  Roy ...................................... 260/932

FOREIGN PATENT DOCUMENTS 777718  6/1957  United Kingdom.

OTHER PUBLICATIONS

Chemical Abstracts, vol. 64 (1966), p. 15925d.
Richard et al., J. Am. Chem. Soc., vol. 83, (1961) pp. 1722-1726.

Primary Examiner—V. D. Turner
Attorney, Agent, or Firm—Hammond & Littell

[57] ABSTRACT

Alkane diphosphonic acid esters having the formula

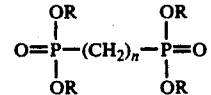

wherein R is a straight- or branched-chain alkyl radical having 1 to 6 carbon atoms; and $n$ is an integer of 1 to 6 are deodorants in anhydrous cosmetic preparations for the suppression of body odor.

17 Claims, No Drawings

COSMETIC DEODORANT PREPARATIONS CONTAINING ALKANE DIPHOSPHONIC ACID ESTERS

FIELD OF THE INVENTION

The present invention relates to the use of alkane diphosphonic acid esters as deodorants in cosmetic preparations for suppressing body odor.

BACKGROUND OF THE INVENTION

It is known that the unpleasant odor accompanying human perspiration is caused by the bacterial decomposition of the sweat which, in the first instance, is odorless. There has been no lack of proposals for countering this disadvantage, although there has hitherto been no fully satisfactory solution. In the main, two methods have been adopted for solving this problem, one being the use of antimicrobial compounds for killing the bacterial skin flora which cause the decomposition of the sweat, and the other being the use of compounds which prevent the secretion of sweat. In addition to this, agents having purely sorptive action and agents for masking the odor play a fully subordinate part. In contrast to the antiperspirants, the cosmetic agents having a deodorizing effect are, without exception, agents having a content of antimicrobial substances. Substances of this type which have been proposed, and some of which have also been used, were, for example, phenol derivatives both containing and not containing halogen, organic mercury compounds, quaternary ammonium compounds, and amino acid derivatives having a disinfecting action. Although the risk of skin irritation is not as high when using deodorants as when using antiperspirants, occasional incompatibility, sensitivity to light and toxic side effects also occur to differing extents with the continuous use of deodorants containing antimicrobial agents. Furthermore, the majority of these products are not odorless, and many of them have a slightly phenolic odor. Thus, there has been an endeavor to produce cosmetic agents which have a satisfactory deodorizing effect, and which have a neutral odor and are largely free from adverse side effects.

OBJECTS OF THE INVENTION

An object of the present invention is the development of a cosmetic preparation which has a satisfactory deodorizing effect, a neutral odor and is largely free from adverse side effects.

Another object of the present invention is the development of a cosmetic deodorant preparation containing alkane diphosphonic acid esters of the formula

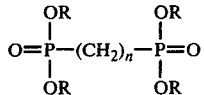

in which R is a straight or branched-chain alkyl radical having 1 to 6 carbon atoms, and n is an integer of 1 to 6.

A further object of the present invention is the development of a cosmetic preparation consisting essentially of from 0.1 to 10% by weight of the above alkane diphosphonic acid ester and the remainder customary cosmetic constituents.

A still further object of the present invention is the improvement in the process of suppressing body odor by utilizing a cosmetic preparation which contains 0.1 to 10% of the above alkane diphosphonic acid ester.

These and other objects of the invention will become more apparent as the description thereof proceeds.

DESCRIPTION OF THE INVENTION

The above objects have been achieved by using alkane diphosphonic acid esters of the following general formula as deodorants in anhydrous cosmetic preparations for the suppression of body odor:

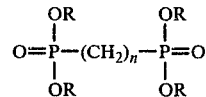

in which R is a straight-chain or branched-chain alkyl radical having 1 to 6 carbon atoms, and n is an integer of 1 to 6. Preferably R has 1 to 4 carbon atoms and n is 1 or 2.

During storage of such products, it is desirable for stability purposes that the cosmetic preparations in accordance with the invention should be anhydrous. Water contents of up to 5% can be tolerated in special cases, according to the ester used and the stability requirements. For the purpose of the present invention, such formulations having a low water content are also considered to be anhydrous.

The alkane diphosphonic acid esters to be used in accordance with the invention can be produced by various methods described in detail in the technical literature. Thus, the production of methylene diphosphonic acid tetraethylester by reacting triethyl phosphite with methylene is described by Ford-Moore and Williams in J. Chem. Soc., 1465 (1947). The production of various tetraalkylesters of methylene diphosphonic acid, such as the methylene diphosphonic acid tetraethylester, and tetrabutylester, by reacting the sodium salt of a dialkylphosphite with a dialkylester of chloromethylene phosphonic acid, is described K. A. Petrov et al. in Zhurnal Obshchei Khimii, Vol. 30, No. 5, pages 1602–1608 (1960). Further information concerning the production of the products to be used in accordance with the invention, such as methylene diphosphonic acid tetraethylester, and -tetra-n-butylester, ethane-1,2-diphosphonic acid tetra-n-butyl-ester, propane-1,3-diphosphonic acid tetra-n-butylester, hexane-1,6-diphosphonic acid tetra-n-butylester is given in the treatise by J. J. Richard et al. in J. Am. Chem. Soc. 83, 1722 ff. (1961). The production of the corresponding esters of branched-chain alcohols, such as methylene diphosphonic acid tetraisopropylester and -sec-butyl-ester, is described in U.S. Pat. No. 3,251,907. The alkane diphosphonic acid esters to be used in accordance with the invention can be obtained without difficulty in conformity with the methods given in the aforesaid references and by Houben-Weyl 12/1, 438 (1963).

Examples of alkane diphosphonic acid esters to be used in accordance with the invention are methylene diphosphonic acid-tetramethyl-ester, methylene diphosphonic acid-tetraethylester, methylene diphosphonic acid-tetrapropylester, methylene diphosphonic acid-tetraisopropylester, methylene diphosphonic acid-tetra-n-butylester, methylene diphosphonic acid-tetra-sec-butylester, and methylene diphosphonic acid-tetrahexylester; ethane-1,2-diphosphonic acid-tetraethylester, ethane-1,2-diphosphonic acid-tetraisopropylester, ethane-1,2-diphosphonic acid-tetra-n-butylester; propane-1,3-diphosphonic acid-tetraethylester, propane-1,3-diphosphonic acid-tetraisopropylester, and propane-1,3-diphosphonic acid-tetra-n-butylester; butane-1,4-diphosphonic acid-tetraethylester, butane-1,4-diphosphonic acid-tetraisopropylester, and butane-1,4-diphosphonic acid-tetra-n-butylester; pentane-1,5-diphosphonic acid-tetramethylester, pentane-1,5-diphosphonic acid-tetraethylester, pentane-1,5-diphosphonic-acid-tetraisopropylester, and pentane 1,5-diphosphonic-acid-tetra-n-butylester; hexane-1,6-diphosphonic acid-tetraethylester, hexane-1,6-diphosphonic acid-tetraisopropylester, and hexane-1,6-diphosphonic acid-tetra-n-butylester.

The alkane diphosphonic acid esters to be used in accordance with the invention can be incorporated in all anhydrous preparations, or preparations having a low water content, which are conventionally used for deodorants, such as powder, pencils, roll-on and sprays, the use of the deodorant spray utilizing a propellant gas being preferred. Incorporation is effected in a known manner by simple mixing or dissolving in other components of the preparation, such as solvents, waxes, fatty substances, polyglycols, and powder bases. The quantities of alkane diphosphonic acid esters, which are incorporated in the cosmetic compositions of the invention, are from 0.1 to 10 percent by weight, preferably 0.5 to 3 percent by weight, relative to the total composition.

Preferably, the alkane diphosphonic acid esters of the invention are used as the sole effective deodorizing substances in the deodorizing cosmetic preparations, although it is possible to combine them with other effective deodorizing substances.

Particularly important among the alkane diphosphonic acid esters are the tetraesters of methylene diphosphonic acid and ethane-1,2-diphosphonic acid; more particularly the tetraethyl-, tetraisopropyl-, and tetraisobutyl-esters, in view of their effectiveness and ready accessibility. The tetraethyl and tetraisopropyl esters of both methylene diphosphonic acid and of ethane-1,2-diphosphonic acid have displayed especially good deodorizing activity.

The products constitute colorless, high-boiling liquids which are odorless or which have only a slight and not unpleasant odor and which can be readily incorporated into all types of cosmetic preparations. Such cosmetic preparations can be readily perfumed.

In contrast to the products generally used as deodorants, the alkane diphosphonic acid esters to be used in accordance with the invention do not have any inhibiting effect with respect to conventional test germs such as Staphylococcus aureus, Echerichia coli, Pseudomonas aeruginosa, Candida albicans, Staphylococcus epidermidis, even in high test concentrations of 5%. Thus, on the basis of known principles, a deodorizing effect was not to be anticipated. Consequently, it was all the most unexpected that, in a panel test, the odor of sweat could be greatly reduced by applying the alkane diphosphonic acid esters used in accordance with the invention.

The invention is now further illustrated by the following examples. These examples are preferred embodiments of the invention and are not to be construed in limitation thereof.

TESTS

The following compounds of the invention were chosen for carrying out the tests described below:

(A) Methylene diphosphonic acid tetraethylester
(B) Methylene diphosphonic acid tetraisopropylester
(C) Methylene diphosphonic acid tetraisobutylester
(D) Ethane-1,2-diphosphonic acid tetraethylester
(E) Ethane-1,2-diphosphonic acid tetraisopropylester
(F) Ethane-1,2-diphosphonic acid tetraisobutylester
(G) Propane-1,3-diphosphonic acid tetraethylester
(H) Propane-1,3-diphosphonic acid tetra-n-butylester
(J) Butane-1,4-diphosphonic acid tetraisopropylester
(K) Hexane-1,6-diphosphonic acid tetra-n-butylester The in-vivo panel tests were carried out in the following manner:

A piece of soap, which did not contain any substances having antimicrobial effectiveness, was given to each of 12 test persons with the instructions to use this soap during the entire test period (3 weeks) and not to use any other soaps, deodorants, antiperspirants or perfume. During the first week, which served as a preparatory week, an uncontrolled wash was carried out with the prescribed soap. During the following week, a shoulder wash, supervised by a supervisor, was carried out each morning under standardized conditions. The spray (test spray) containing the active substance was applied under the left shoulder of six test persons and under the right shoulder of six test persons. A comparison spray was sprayed under the other shoulder in each case. The test spray and the comparison spray were each sprayed under the shoulder for 2 seconds from a distance of 15 cm. The application sides were changed during the third test week.

After the spray had been applied and the solvent had evaporated, shoulder pads were secured below the shoulders of the persons being tested by means of rubber bands and had to be worn for a period of 8 hours. For the purpose of assessing the odor, the shoulder pads were removed after expiration of the test period (8 hours), placed into coded, sealable glass containers heated to 37° C., and the sealed glasses were subsequently stored for 15 minutes at 37° C. The difference between the left and right shoulder pads of each person being tested was assessed by three trained odor testers who gave their assessments independently of one another. Each tester received a fresh test form for each test day and supplied his assessment in accordance with the following scheme:

5 points — no body odor
4 points — body odor just perceptible
3 points — distinct body odor
2 points — strong body odor
1 point — strong unpleasant odor of sweat The assessments "better, worse or the same" were determined by a test director from these assessments of the left-right samples (test spray/comparison spray) and were statistically evaluated in accordance with the four field test ( )($^2$ test, Statistische Auswertungsmethoden, L. Sachs, Springer-Verlag Berlin (1969), pages 341–364).

Monday, the first day on which the spray was applied in each case, was not taken into account in the evaluation in the two test weeks (weeks 2 and 3). The effectiveness of the alkane diphosphonic acid esters of the invention is evident from the summary of test results in the Table presented hereinafter.

The test sprays used in the tests had the following composition:
Solution of effective substance:
X % effective substance
10 % isopropanol
and 100−(10+X)% ethanol Test spray composition:
40 parts by weight of effective substance solution
60 parts by weight of dichlorodifluoromethane X = 1.25 in the case of compound D (Test No. 5 below)
X = 5 in the case of compounds A, D, G (Tests No. 1, 4 and 8 below)
X = 6.25 in the case of compounds B, E, H, J (Tests No. 2, 6, 9, and 10 below)
X = 3.75 in the case of compounds C and F (Tests No. 3 and 7 below)
X = 7.5 in the case of compound K (Test No. 11 below)

The comparison spray used in the tests had the following composition:
Solution:
10% Isopropanol
90% Ethanol
Comparison spray composition:
40 parts by weight of the solution
60 parts by weight of dichlorodifluoromethane Summary of test results

| Test No. | Test time in days | Concentration of effective substance of test spray % compound | Significance of positive deodorizing effect in % statistical certainty according to ($^2$ - four field test) |
|---|---|---|---|
| 1 | 8 | 2 % A | 99 |
| 2 | 8 | 2.5 % B | 99 |
| 3 | 8 | 1.5 % C | 90 |
| 4 | 8 | 2 % D | 99 |
| 5 | 8 | 0.5 % D | 90 |
| 6 | 8 | 2.5 % E | 99 |
| 7 | 8 | 1.5 % F | 90 |
| 8 | 8 | 2 % G | 90 |
| 9 | 8 | 2.5 % H | 90 |
| 10 | 8 | 2.5 % J | 90 |
| 11 | 8 | 3 % K | 90 |

EXAMPLES

Some examples of basic formulations for cosmetic preparations having a deodorizing effect are given hereinafter and can be produced by using the alkane diphosphonic acid esters of the invention. The compounds mentioned hereinafter can be replaced with equally good results by other alkane diphosphonic acid esters in accordance with the invention, and the quantity of effective substance can also be varied.

EXAMPLE 1

| Deodorizing Pencil | |
|---|---|
| 2-octyldodecanol | 28.0 parts by weight |
| Cetylstearylalcohol | 3.0 parts by weight |
| Sodium stearate | 8.0 parts by weight |
| Coconut fatty acid monoethanolamide | 3.0 parts by weight |
| Paraffin oil | 3.0 parts by weight |
| Propylene glycol | 2.0 parts by weight |
| Ethanol | 50.0 parts by weight |
| Ethane-1,2-diphosphonic acid tetrahethylester | 3.0 parts by weight |

EXAMPLE 2

| Deodorizing Powder | |
|---|---|
| Rice starch derivative NAL R-5 | 12.0 parts by weight |
| Magnesium carbonate | 2.0 parts by weight |
| Zinc oxide | 2.0 parts by weight |
| Talc, extra fine | 79.0 parts by weight |
| Hexane-1,65-diphosphonic acid tetra-n-butylester | 5.0 parts by weight |

EXAMPLE 3

| Deodorizing Spray | |
|---|---|
| Ethanol | 30.0 parts by weight |
| Isopropanol | 6.8 parts by weight |
| Propylene glycol | 1.2 parts by weight |
| Methylene diphosphonic acid tetraethylester | 2.0 parts by weight |
| Dichlorodifluoromethane/ dichlorotetrafluoroethane (60:40) | 60.0 parts by weight |

EXAMPLE 4

| Deodorizing Spray | |
|---|---|
| Ethanol | 12.0 parts by weight |
| Isopropanol | 18.0 parts by weight |
| Isopropylmyristate | 2.0 parts by weight |
| Methylene disphosphonic acid tetraisobutylester | 3.0 parts by weight |
| Dichlorodifluoromethane/ dichlorotetrafluoroethane(60:40) | 65.0 parts by weight |

EXAMPLE 5

| Deodorizing Spray | |
|---|---|
| Caprylic/capric acide triglyceride | 4.0 parts by weight |
| Isopropanol | 4.0 parts by weight |
| Methylene diphosphonic acid tetraisopropylester | 3.0 parts by weight |
| Dichlorodifluoromethane/ dichlorotetrafluoroethane(60:40) | 89.0 parts by weight |

EXAMPLE 6

| Deodorizing Spray | |
|---|---|
| Propylene glycol | 1.5 parts by weight |
| Isopropylstearate | 1.5 parts by weight |
| Ethane-1,2-diphosphonic acid tetraisopropylester | 2.5 parts by weight |
| Ethanol | 12.5 parts by weight |
| Dichlorodifluoromethane/ dichlorotetrafluoroerthane(60:40) | 82.0 parts by weight |

EXAMPLE 7

| Deodorizing Spray | |
|---|---|
| Propylene glycol | 2.0 parts by weight |
| Isopropylmyristate | 2.0 parts by weight |
| Ethanol | 16.0 parts by weight |
| Propane-1,3-diphosphonic acid tetraethylester | 5.0 parts by weight |
| Trichlorofluoromethane/ dichlorodifluoromethane(50:50) | 75.0 parts by weight |

EXAMPLE 8

| Deodorizing Spray | |
|---|---|
| Ethanol | 30.0 parts by weight |
| Isopropanol | 7.0 parts by weight |
| Propylene glycol | 2.0 parts by weight |

| -continued | |
| --- | --- |
| Deodorizing Spray | |
| Methylene diphosphonic acid tetraethylester | 1.0 parts by weight |
| Dichlorodifluoromethane/ dichlorotetrafluoroethane(60:40) | 60.0 parts by weight |

EXAMPLE 9

| Deodorizing Spray | |
| --- | --- |
| Ethanol | 32.0 parts by weight |
| Isopropylmyristate | 3.0 parts by weight |
| Butane-1,4-diphosphonic acid tetraisopropylester | 5.0 parts by weight |
| Dichlorodifluoromethane | 60.0 parts by weight |

EXAMPLE 10

| Deodorizing Spray | |
| --- | --- |
| Isopropylmyristate | 3.0 parts by weight |
| Ethanol | 24.0 parts by weight |
| Isopropanol | 10.0 parts by weight |
| Ethane-1,2-diphosphonic acid tetraisobutylester | 3.0 parts by weight |
| Trichlorofluoromethane/ dichlorodifluoromethane(50:50) | 60.0 parts by weight |

We claim:

1. A method of suppressing human body odor by applying to the areas of concentrated sweat glands a safe but deodorizing amount of a cosmetic preparation which contains 0.1 to 10% of an alkanediphosphonic acid ester of the general formula

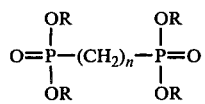

in which R is a straight- or branched-chain alkyl radical having 1 to 6 carbon atoms and n is an integer of 1 to 6, and the remainder customary cosmetic constituents.

2. The method of claim 1 in which said ester is present in a quantity of from 0.5 to 3 percent by weight, relative to the total cosmetic preparation.

3. The method of claim 1 in which the alkanediphosphonic acid ester is an ester of methylene diphosphonic acid or ethane-1, 2-diphosphonic acid.

4. The method of claim 3 in which the alkanediphosphonic acid ester is a tetraethyl-, tetraisopropyl or tetraisobutylester.

5. The method of claim 4 in which the alkanediphosphonic acid ester is a tetraethyl- or tetraisopropyl-ester.

6. The method of claim 1 in which the alkanediphosphonic acid ester is a member selected from the group consisting of methylene diphosphonic acid tetraethylester, methylene diphosphonic acid tetraisopropylester, methylene diphosphonic acid tetraisobutylester, ethane-1, 2-diphosphonic acid tetraethylester, ethane-1,2-diphosphonic acid tetraisopropylester, ethane-1, 2-diphosphonic acid tetraisobutylester, propane-1,3-diphosphonic acid tetraethylester, propane-1, 3-diphosphonic acid tetra-n-butylester, butane-1,4-diphosphonic acid tetraisopropylester, and hexane-1,6-diphosphonic acid tetra-n-butylester.

7. The method of claim 1 in which the alkanediphosphonic acid ester is methylene diphosphonic acid tetraethylester.

8. The method of claim 1 in which the alkanediphosphonic acid ester is methylene diphosphonic acid tetraisopropyl ester.

9. The method of claim 1 in which the alkanediphosphonic acid ester is ethane-1,2-diphosphonic acid tetraethylester.

10. The method of claim 1 in which the alkanediphosphonic acid ester is ethane-1,2-diphosphonic acid tetraisopropyl ester.

11. The method of claim 1 in which the alkanediphosphonic acid ester is ethane-1,2-diphosphonic acid tetraisobutylester.

12. The method of claim 1 in which the alkanediphosphonic acid ester is methylene diphosphonic acid tetraisobutylester.

13. The method of claim 1 in which the cosmetic preparation is in the form of a powder, pencil, roll-on or spray.

14. The method of claim 1 in which the cosmetic preparation is in the form of a deodorant spray and has a content of a propellant gas.

15. The method of claim 1 in which R is a straight-chain or branched-chain alkyl radical having 1 to 4 carbon atoms and n is 1 or 2.

16. The method of claim 1 in which the customary cosmetic constituents are selected from the group consisting of solvents, waxes, fatty substances, polyglycols, perfumes, and powder bases.

17. A substantially anhydrous cosmetic deodorant preparation in the form of a deodorant spray, comprising 0.1 to 10% by weight, relative to the total cosmetic preparation, of an alkanediphosphonic acid ester of the general formula

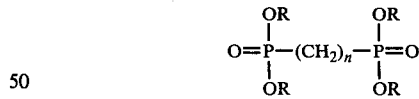

in which R is a straight-chain or branched-chain alkyl radical having 1 to 6 carbon atoms and n is an integer of 1 to 6, and the remainder customary cosmetic constituents and a propellant gas.

* * * * *